United States Patent
Zar et al.

(10) Patent No.: US 9,460,309 B2
(45) Date of Patent: Oct. 4, 2016

(54) SECURITY POUCH FOR AN ELECTRONIC DEVICE

(71) Applicant: Peeled Group LLC, Aptos, CA (US)

(72) Inventors: Randy J. Zar, Aptos, CA (US); Aaron Zar, San Jose, CA (US)

(73) Assignee: PEELED GROUP LLC, Encinitas, CA (US)

( * ) Notice: Subject to any disclaimer, the term of this patent is extended or adjusted under 35 U.S.C. 154(b) by 0 days.

(21) Appl. No.: 14/479,067

(22) Filed: Sep. 5, 2014

(65) Prior Publication Data

US 2015/0052617 A1 Feb. 19, 2015

Related U.S. Application Data

(63) Continuation-in-part of application No. 13/465,787, filed on May 7, 2012, now abandoned.

(60) Provisional application No. 61/483,572, filed on May 6, 2011.

(51) Int. Cl.
| | |
|---|---|
| *B65D 33/00* | (2006.01) |
| *G06F 21/62* | (2013.01) |
| *A45C 11/00* | (2006.01) |
| *H04B 1/3888* | (2015.01) |

(52) U.S. Cl.
CPC ............ *G06F 21/6245* (2013.01); *A45C 11/00* (2013.01); *B65D 33/00* (2013.01); *H04B 1/3888* (2013.01); *A45C 2011/002* (2013.01); *A45F 2200/0516* (2013.01)

(58) Field of Classification Search
CPC .............. G06F 21/6245; A45C 11/00; A45C 2011/002; A45F 2200/0516; B65D 33/00; B65D 33/2541; H04B 1/3888; H05K 9/0043

USPC ................ 206/305, 320, 720–725; 174/350, 174/372–382, 386; 383/63, 65, 107–109
See application file for complete search history.

(56) References Cited

U.S. PATENT DOCUMENTS

| | | | | |
|---|---|---|---|---|
| 3,381,592 A | * | 5/1968 | Ravel | 383/63 |
| 4,593,736 A | | 6/1986 | Morita | |
| 6,139,188 A | * | 10/2000 | Marzano | 383/63 |
| 7,075,798 B2 | | 7/2006 | Hendrickson | |
| 7,596,850 B2 | * | 10/2009 | Barth et al. | 29/594 |
| 7,601,921 B2 | * | 10/2009 | Schroader | 174/372 |
| 8,270,929 B1 | | 9/2012 | Koeppel | |
| 8,479,922 B2 | | 7/2013 | Kennedy | |
| 8,859,913 B2 | * | 10/2014 | Judy | H05K 9/0043 206/720 |
| 8,878,080 B2 | * | 11/2014 | Judy et al. | 174/378 |
| 2006/0196792 A1 | | 9/2006 | Barth | |
| 2007/0034406 A1 | | 2/2007 | Schroader | |
| 2011/0290676 A1 | | 12/2011 | Kershenstein | |

(Continued)

FOREIGN PATENT DOCUMENTS

| | | |
|---|---|---|
| EP | 1981324 B1 | 4/2011 |
| WO | WO2012122076 A1 | 9/2012 |

*Primary Examiner* — Bryon Gehman
(74) *Attorney, Agent, or Firm* — David R. Stevens; Stevens Law Group

(57) ABSTRACT

Provided is a pouch for covering a mobile device to block electronic signals and/or provide and antibacterial function. In one example, a pouch includes a shield configured to envelope the mobile device, a covering configured to envelope the shield, and a seal composed of offset rib structures configured to fully encase the mobile device in order to prevent electronic signals from reaching the device.

19 Claims, 8 Drawing Sheets

(56) References Cited

U.S. PATENT DOCUMENTS

2012/0047631 A1    3/2012  Connolly
2012/0061134 A1*   3/2012  Kennedy .................. 174/377
2012/0114270 A1    5/2012  Roberts
2013/0118935 A1*   5/2013  Zar ........................... 206/320

* cited by examiner

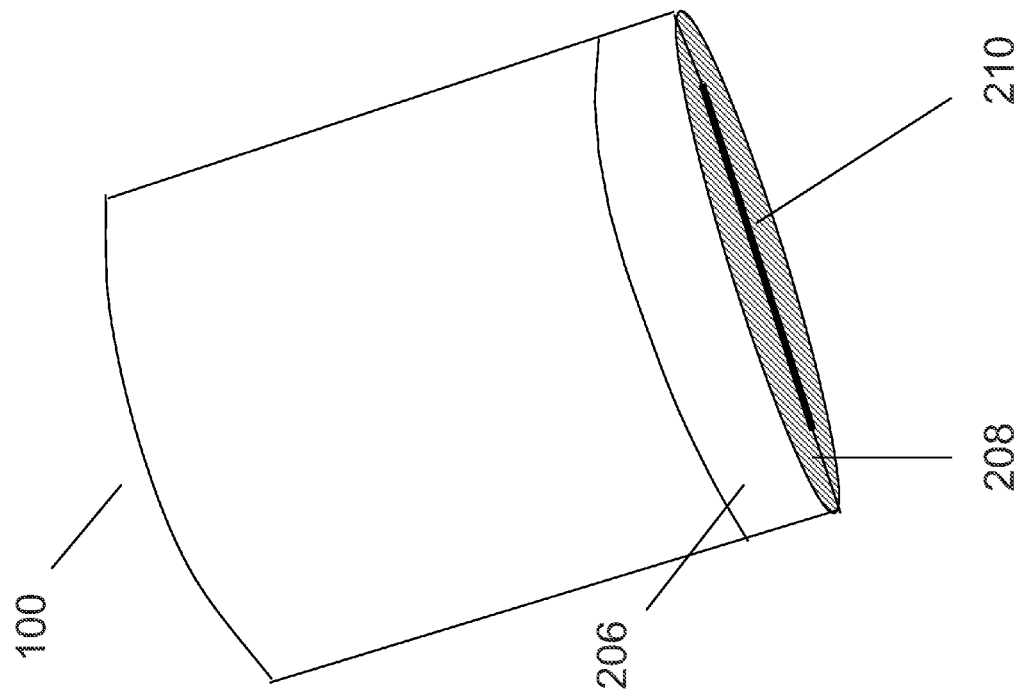
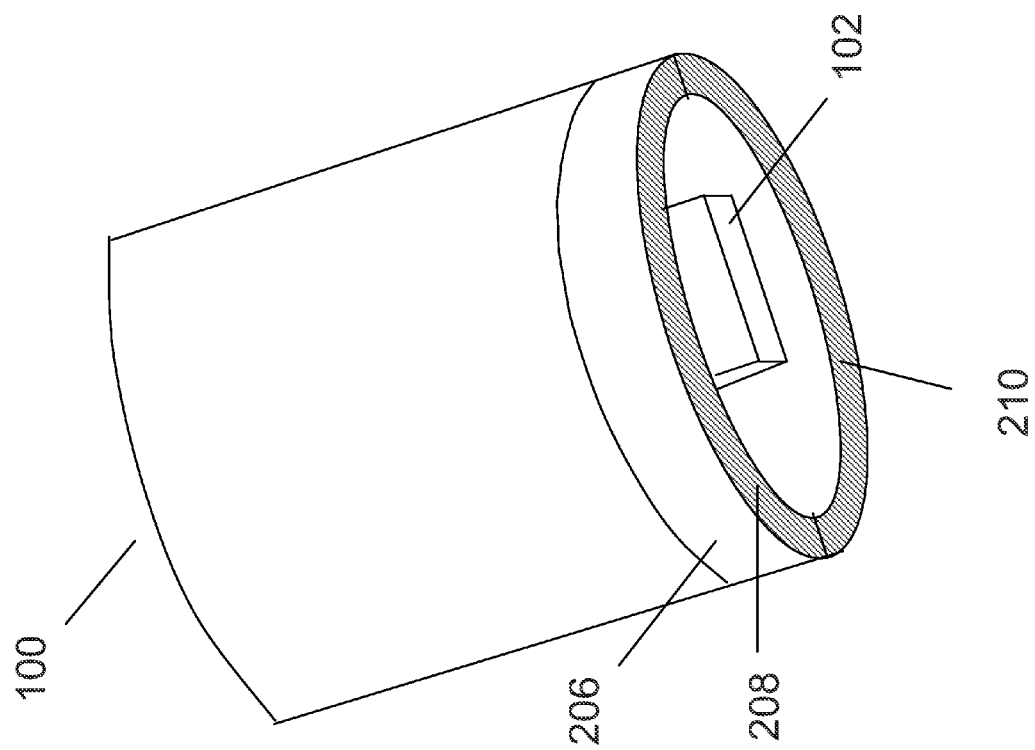

SECURITY POUCH FOR AN ELECTRONIC DEVICE

CROSS-REFERENCE TO RELATED APPLICATIONS

This application claims the benefit of U.S. Provisional Application Ser. No. 61/483,572, filed May 6, 2011, which is hereby incorporated herein by reference in its entirety. This application is also a Continuation in Part of U.S. application Ser. No. 13/465,787, filed May 7, 2012, which is hereby incorporated herein by reference in its entirety.

BACKGROUND

Mobile devices have never been so indispensable in human life and, for the same reason, have posed a number of new concerns. Recently it has been brought to public attention that some mobile devices are able to track and record their users' locations through a Wi-Fi network, even while these devices are powered off. Examples of such devices include but are not limited to Apple's iPhone® and iPad®, Google's Android® Motorola® phones, RIM's Blackberry™ phones, Samsung's Galaxy™ phones, Microsoft's Windows®, and other phones. Mobile devices are able to track and record their users' locations using, for example, the GPS functionality in the device. Further, mobile devices can be hacked into, leaving the users' personal data vulnerable to theft. The ability of an intruder to access the camera of a mobile device or record a phone conversation underscores the concerns of intrusion to privacy and security.

Furthermore, the alleged solution of turning off the tracking function is not necessarily reassuring. It must be noted that the makers of above high end mobile devices did not give consumers any notice regarding the tracking and recording of user location data. Thus, it raises the question whether turning off the tracking function really disables the tracking or it is merely a marketing technique to soothe fears. It is also uncertain as to whether the mobile device makers have other applications of the different wireless networking protocols that are available to the user of a mobile device, such as Bluetooth, Near Field Communication (NFC) and Wi-Fi network technology that are not made public and have yet to be discovered. Therefore, it is desirable to have a physics-based solution that is easy to operate and reassures the tracking is disabled.

In addition, a mobile device is one of the most often touched devices and imposes a notable risk to the user's health, in view of the threats of viral diseases caused by infections. Mobile devices carry germs, viruses and bacteria. At the same time, they are usually held by hands and close to the user's ears, face, and mouth. Yet, the market has not seen a device that is portable, convenient to use, and has an appealing appearance for everyday carrying. Therefore, a simple, convenient and affordable solution is needed for sanitizing a mobile device.

Hence, it is desirable to have a solution that solves both of the above problems. As will be seen, the invention provides such a solution in an elegant manner.

BRIEF DESCRIPTION OF THE DRAWINGS

FIGS. 2A and 2B illustrate the open and closed positions of the embodiment.

DETAILED DESCRIPTION

Figure 1:
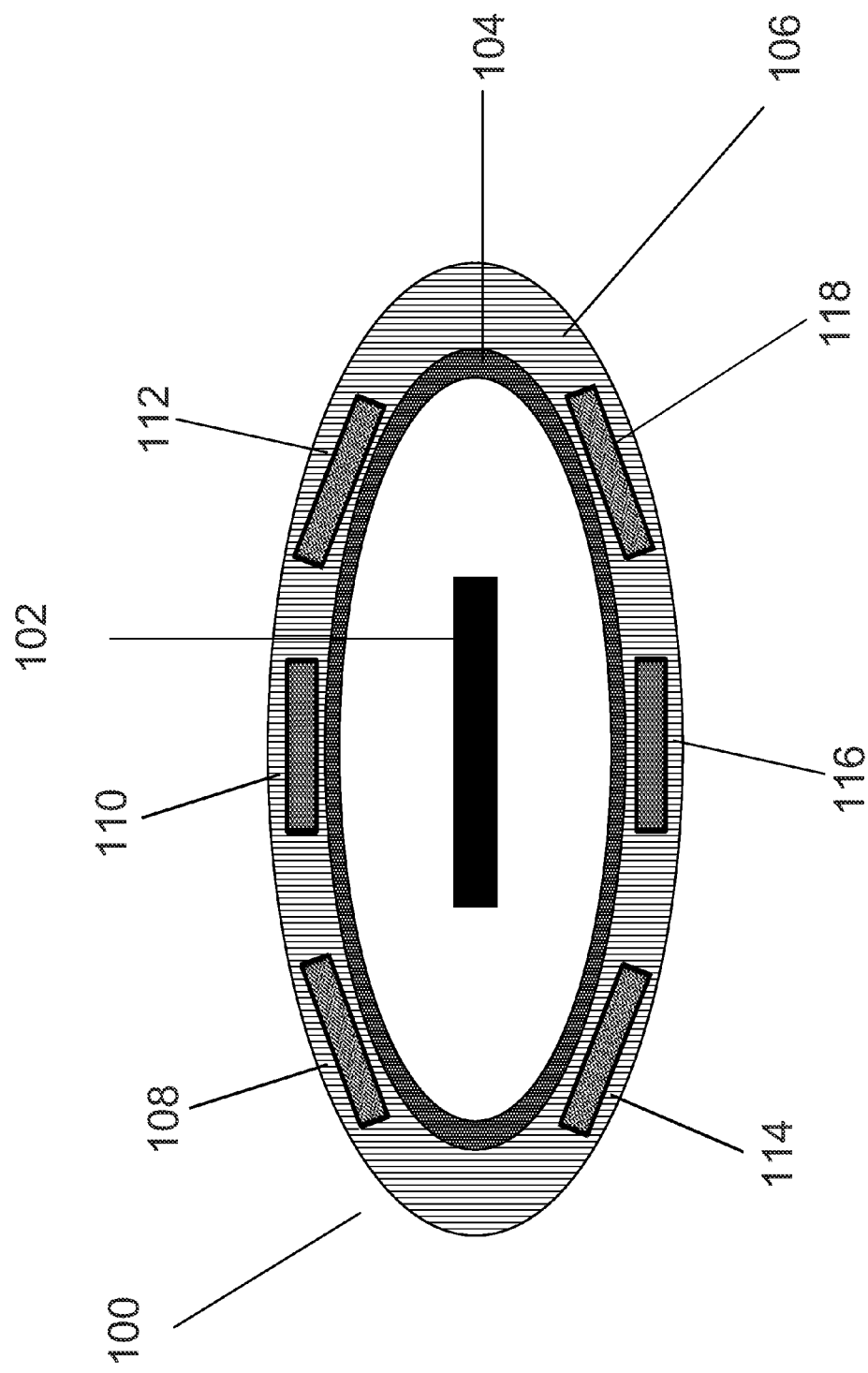
FIG. 1 illustrates an embodiment of the invention.

The invention is directed to a security pouch or other structure for holding an electronic device, such as a mobile device, shielding it from electronic signals and/or sanitizing the device. There are various embodiments and examples possible, and those skilled in the art will appreciate that, given this disclosure, many embodiments and examples may be configured within the invention. The examples included herein are intended as exemplary, and in no way limit the invention, but are provided for illustration and understanding.

Particular examples discussed herein refer to the ability of the security pouch to shield a mobile device from various electronic signals. The same security pouch is also useful to shield other items that may send or receive electronic signals, such as passports with RFID chips, credit cards with RFID chips, and any other device with an RFID chip (e.g., security badges, transportation passes, and the like). Additionally, any other item capable of sending or receiving electronic signals may be inserted into the security pouch to shield those electronic signals.

In one example, a compartment wall of a security pouch includes at least two layers. An inner layer may include a shield made from a highly electrically conductive material, or other material that serves to block electronic signals, such as for example electromagnetic and/or radio frequency (RF) signals. An outer layer may be a covering made from a commonly used fabric, such as cloth, leather or vinyl.

In a particular embodiment, the security pouch is constructed of eight layers, of which the innermost layer is a liner material, and the next four layers are composed of nickel/copper ripstop shielding material that serves to attenuate a broad spectrum of signals. The sixth layer surrounding the inner four layers could be composed of a material such as an RFID/NFC shielding foil similar to the product sold under the name Cryptalloy™ available from Kryptonic Technologies. The seventh layer is composed of thin foam, while the outermost eighth layer is constructed of a material such as vinyl, leather or canvas. These eight layers are laid flat on top of each other, then sandwiched and permanently sealed on the bottom and the sides. The top opening is sealed by two or more stacking internal ribs or lips covered in shielding material and the opening is mechanically sealed by multiple rare earth magnets.

When the security pouch is closed, the shield closes and is sealed, thereby blocking electronic signals from reaching the mobile device encased inside the shield. Additionally, the closed security pouch blocks the electronic signals emitted by the encased device from exiting the shielded security pouch. The shield also blocks out GPS signals from reaching the electronic device enclosed within, thereby preventing the device from tracking and recording the user's location. In some embodiments, the shield is made from a loaded silver material that serves to sanitize the mobile device by eliminating bacteria.

As a result, a security pouch configured according to the invention may be configured to provide a portable, effective and affordable solution to prevent a mobile device from emitting and receiving electronic signals, thereby making the device untraceable, untrackable and undetectable, while at the same time sanitizing the device. The shield thus effectively provides security from eavesdropping and from unauthorized data extraction from the electronic device.

The described embodiments are not specifically designed to be airtight, watertight or buoyant, although those skilled in the art will note that these features can be added to the embodiments disclosed in this application with appropriate modifications. The two basic functions provided by the disclosed security pouch are device isolation with respect to direct or indirect line-of-sight paths for electronic communication of the protected electronic device with other devices, as well as a sanitization function that disinfects the electronic device that is encased within the security pouch.

The disclosed security pouch is easy to use. A user does not have to physically operate a sealing mechanism such as a zipper, a flap or a Velcro strip in order to access the electronic device when retrieving it from the security pouch or when storing the electronic device in the security pouch. Due to the magnetic self-sealing capability of the pouch provided by the rare earth magnets at the pouch opening, a user can perform a one-handed operation of sliding the electronic device in and out of the security pouch. Furthermore, the electronic signal isolation capability of the security pouch does not depend on the user having to ensure that the opening to the security pouch is securely sealed. In existing devices that use sealing mechanisms such as flaps, Velcro strips and zippers, it is the user's responsibility to ensure that the opening to the security pouch is appropriately closed to prevent any potential signal leakage. The use of rare earth magnets in conjunction with a novel rib structure to seal the opening of the security pouch embodiments disclosed here ensures that the opening to the security pouch is sealed automatically, without requiring any action on the user's part. Additional electronic signal shielding is provided by the sealing magnets themselves, since these magnets serve to provide an additional barrier to electronic signals from both entering and leaving the pouch. In this way, the disclosed invention provides a convenient way of shielding electronic devices.

FIG. 1 shows a cross-section view of one embodiment of a security pouch 100 for holding and encasing a mobile device 102 (or other electronic device). Security pouch 100 includes a shield 104, a covering 106 configured to envelope the shield, and a seal (shown in FIG. 2). Shield 104 is made of a material that has high electrical conductivity, and therefore is capable of shielding electromagnetic fields. Examples of such material include, but are not limited to, gold, silver, zinc, copper and nickel, nickel/copper ripstop, colloidal silver lined ripstop, aluminum, and laminated flexible metals. This embodiment shows six rare earth magnets 108, 110, 112, 114, 116 and 118 across the entirety of the seal. Each cylindrically shaped magnet attracts the corresponding magnet at the opposite side of the opening and these magnets clasp shut due to magnetic attraction, thereby closing the seal. The rare earth magnets 108, 110, 112, 114, 116 and 118 also provide additional isolation from electrical signals by providing an additional layer of signal blockage. Although six rare earth magnets 108-118 are shown in FIG. 1, alternate embodiments may include any number of magnets arranged in any configuration. Further, the rare earth magnets 108-118 shown in FIG. 1 may be any shape or size.

When shield 104 is sealed, mobile device 102 is encased within the shield and effectively blocked from sending or receiving electronic signals. In particular, shield 104 blocks RF signals from a Wi-Fi network, thereby stopping mobile device 102 from pinging or otherwise communicating in a way that reveals its location. As a result, mobile device 102 is disabled from tracking its location or any kind of unidirectional or bidirectional communication with an external device (i.e., a device external to security pouch 100).

FIGS. 2A and 2B show the open and closed positions respectively of the security pouch 100 for holding and encasing mobile device 102. A seal 206 is configured to close the shield and covering to fully encase mobile device 102 to prevent electronic signals from reaching mobile device 102. In some embodiments, the seal 206 may be made using rare earth magnets 108-118 as discussed above. In other embodiments, rare earth magnets may be used on one side of seal 206, and a magnetic material 210 (such as iron, steel or nickel) on the opposite side of seal 206 such that the rare earth magnets are attracted to the magnetic material. In additional embodiments, both strips 208 and 210 can be magnetic strips.

Figure 3:
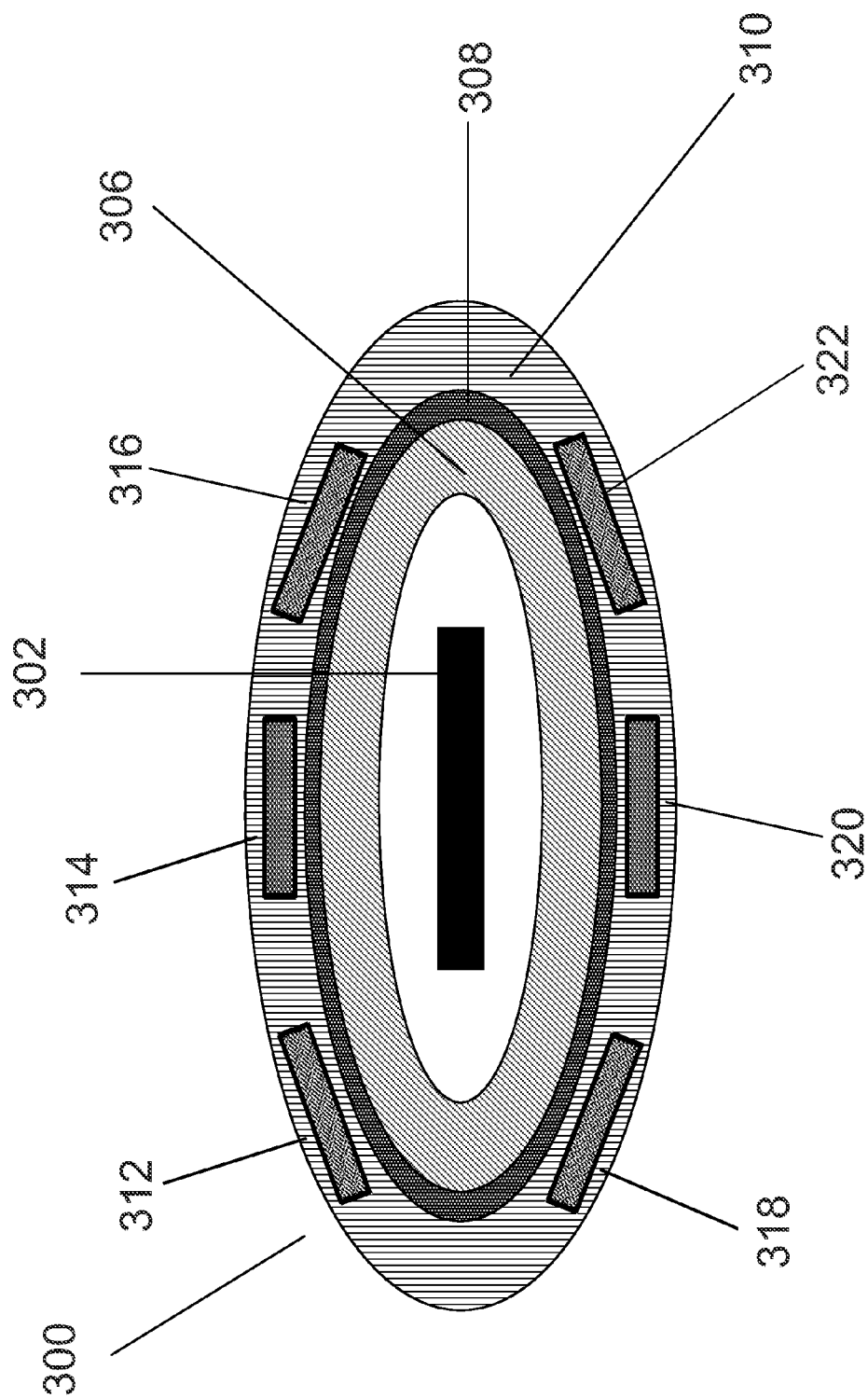
FIG. 3 illustrates another embodiment of the invention.

Referring to FIG. 3, a cross-section view of another embodiment of a security pouch 300 includes three layers: an inner lining 306, a shield 308, and a covering 310. Shield 308 is encased (or enveloped) by inner lining 306, which protects shield 308 from stains, wearing and tearing. This embodiment shows six rare earth magnets 312, 314, 316, 318, 320 and 322 across the opening of security pouch 300. Each magnet 312-322 attracts the corresponding magnet at the opposite end of the pouch opening and these magnets clasp shut due to magnetic attraction, thereby closing the seal. The rare earth magnets 312-322 also provide additional isolation from electrical signals by providing an additional layer of signal blockage. Security pouch 300 fully encases a mobile device 302 to prevent electronic signals from reaching mobile device 302 while also preventing electronic signals emitted by mobile device 302 from leaving the security pouch 300.

Figure 4:
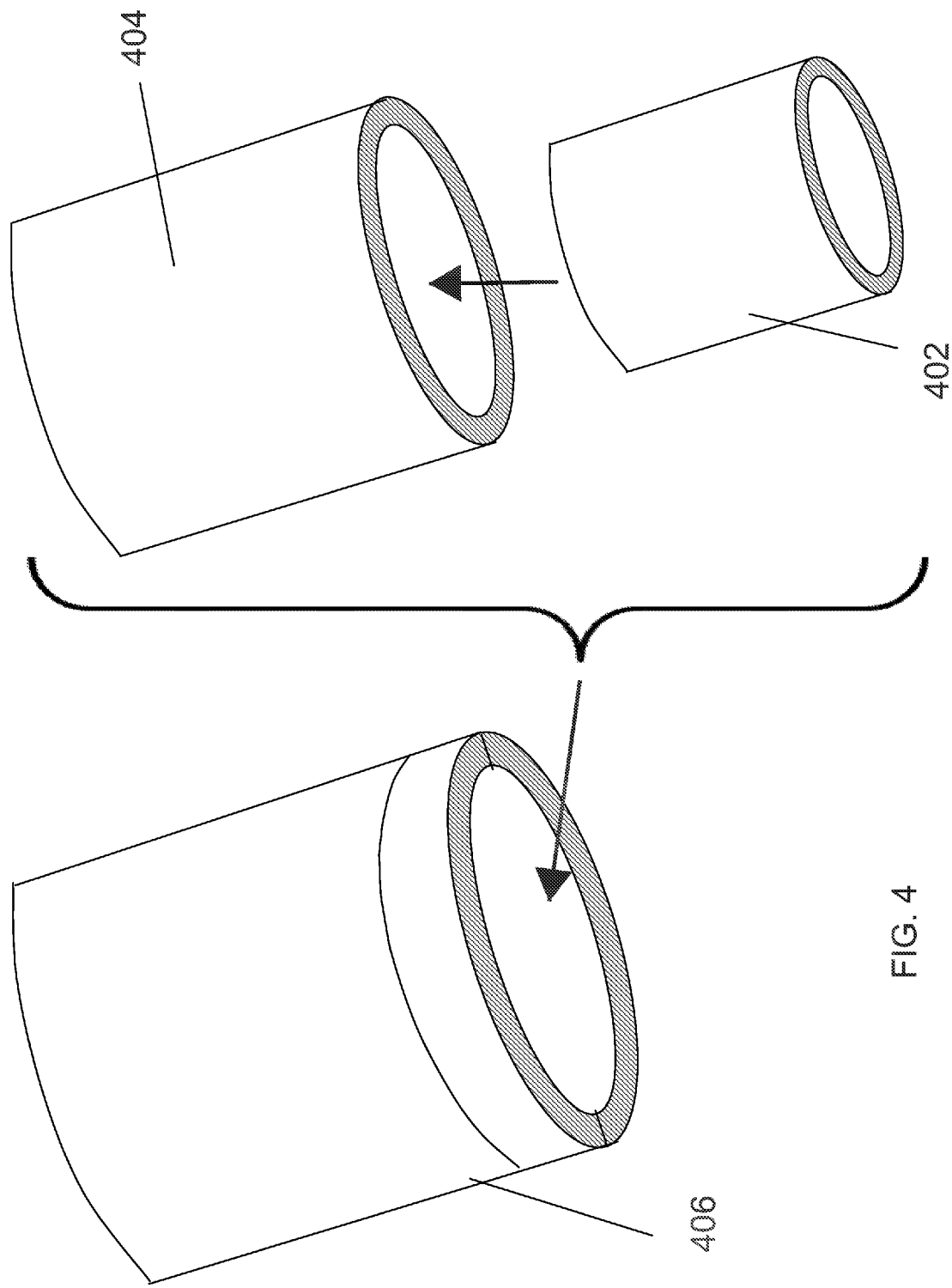
FIG. 4 provides another illustration of the above embodiment.

FIG. 4 illustrates a general view of the three layers (or components) that make up a security pouch of the above embodiments. The three layers include an inner lining 402, a shield 404, and a covering 406. Inner lining 402, shield 404, and covering 406 may be assembled as separate components (as shown in FIG. 4), or the materials used in inner lining 402, shield 404, and covering 406 may be assembled and manufactured simultaneously as a single security pouch.

Figure 5A:
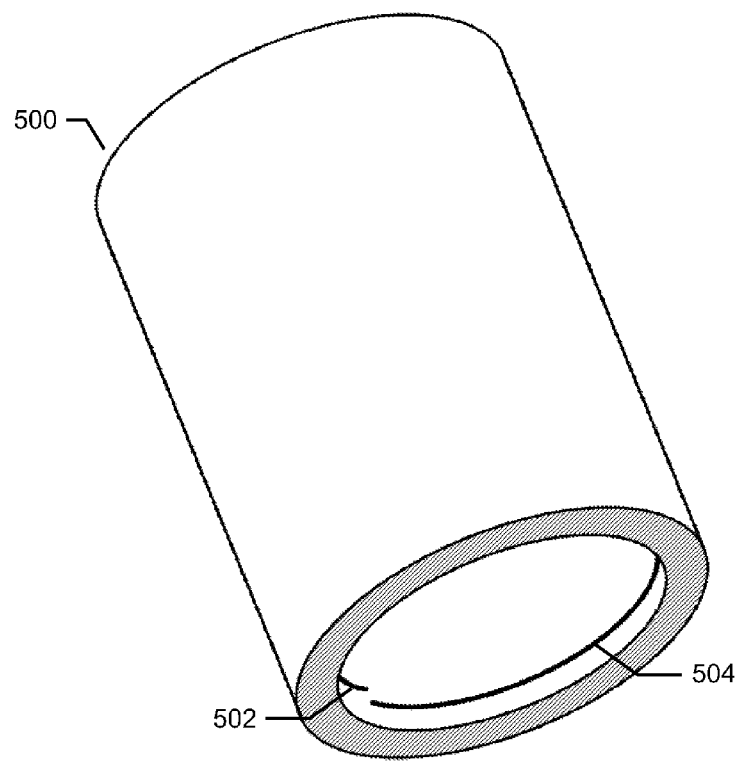
FIGS. 5A and 5B illustrate an embodiment of the invention including an offset rib structure that seals the opening of the security pouch or other device.
Figure 5B:
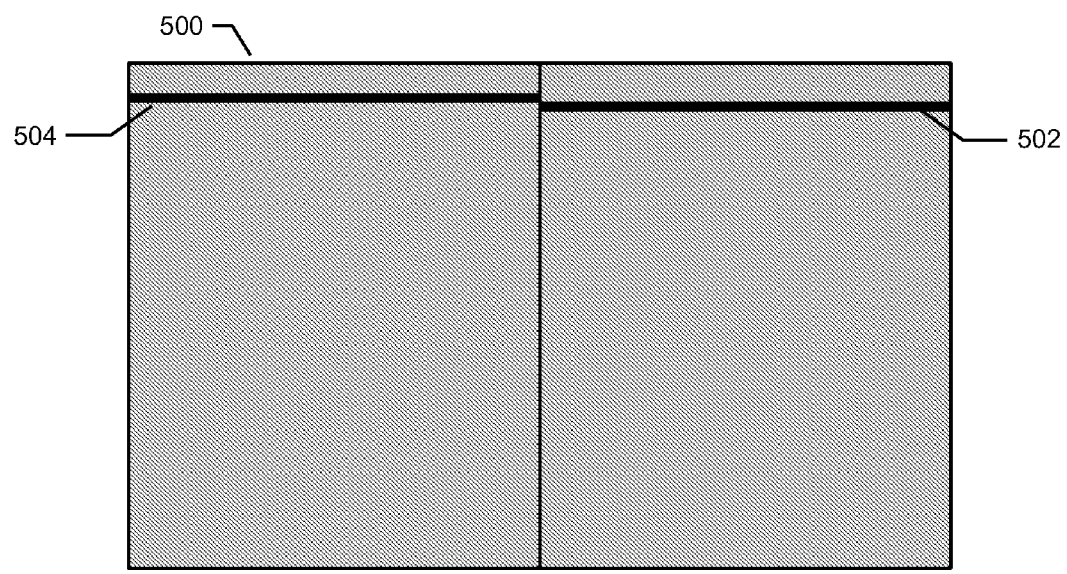

FIG. 5A illustrates another embodiment of a security pouch 500 showing internal rib structures 502 and 504 that form a seal to prevent electronic signals from reaching a mobile device located within security pouch 500. FIG. 5B is another view of the security pouch 500 with one edge opened up to show the internal positions of rib structures 502 and 504. Rib structures 502 and 504 can be of circular cross section, and extend inwardly into the opening within security pouch 500. In example implementations, rib structures 502 and 504 extend inwardly approximately 2.5-5 millimeters into the opening within security pouch 500.

In some embodiments, rib structures 502 and 504 are stacked such that they overlap each other when security pouch 500 is closed. As shown in FIG. 5B, rib structures 502 and 504 are slightly offset, which provides the overlapped arrangement when security pouch 500 is closed. Further, when the opening of the pouch is closed, the rib structures 502 and 504 lay parallel, adjacent to, and in contact with one another, thereby effectively physically sealing the opening of security pouch 500. Electronic signal isolation at the seal is achieved by covering the rib structures 502 and 504 with shielding material, such as the shielding material used for the shield 104 discussed above.

In some embodiments, rib structures 502 and 504 are made from braided cotton rope and covered with two layers of nickel/copper ripstop. In other embodiments, the rib structures 502 and 504 are made from materials such as rolled nickel/copper ripstop, metal wire, braided cord/rope and leather cord. In other embodiments, the rib structures 502 and 504 are magnetic structures covered in shielding material. In this embodiment, additional sealing effectiveness would be provided due to the magnetic closure capability of the rib structures 502 and 504. The rib structures 502 and 504 are an important component of the electronic shielding system; without these rib structures the pouch can only provide isolation from NFC/RFID communication, but is vulnerable to leakage of other RF signals such as WiFi, cellphone signals and so on. In all these embodiments, once security pouch 500 is closed, the seal provides a barrier to electronic signals either entering or leaving the security pouch.

One advantage of using offset stacked rib structures 502 and 504 is that the user does not need to operate a mechanism such a zipper in order to either seal the pouch or to remove the enclosed electronic device. Access to either storing or retrieving a device is easy, as a device can easily be slid in and out of security pouch 500 by separating rib structures 502 and 504 apart from one another. Additionally, the rib structures 502 and 504 help prevent a mobile device from sliding out of security pouch 500. For example, the rib structures 502 and 504 provide a barrier that helps maintain the mobile device within security pouch 500.

In other embodiments, rib structures 502 and 504 can also be made to close magnetically. For example one of the rib structures 502 or 504 is magnetic, while the other rib structure is made of magnetic material, such as iron, steel or nickel. In another embodiment, both rib structures 502 and 504 can be made magnetic. As seen in FIGS. 5A and 5B, rib structures 502 and 504 allow the realization of a robust sealing mechanism. This embodiment provides improved closure and shielding for security pouch 500 by offsetting the magnetic rib structures 502 and 504, which provides increased magnetic contact between the rib structures. This increased magnetic contact adds to the mechanical security of security pouch 500 in addition to the magnetic seal provided by rib structures 502 and 504, rather than solely relying on magnetic attraction (parallel non-offset strips) alone.

Figure 6A:
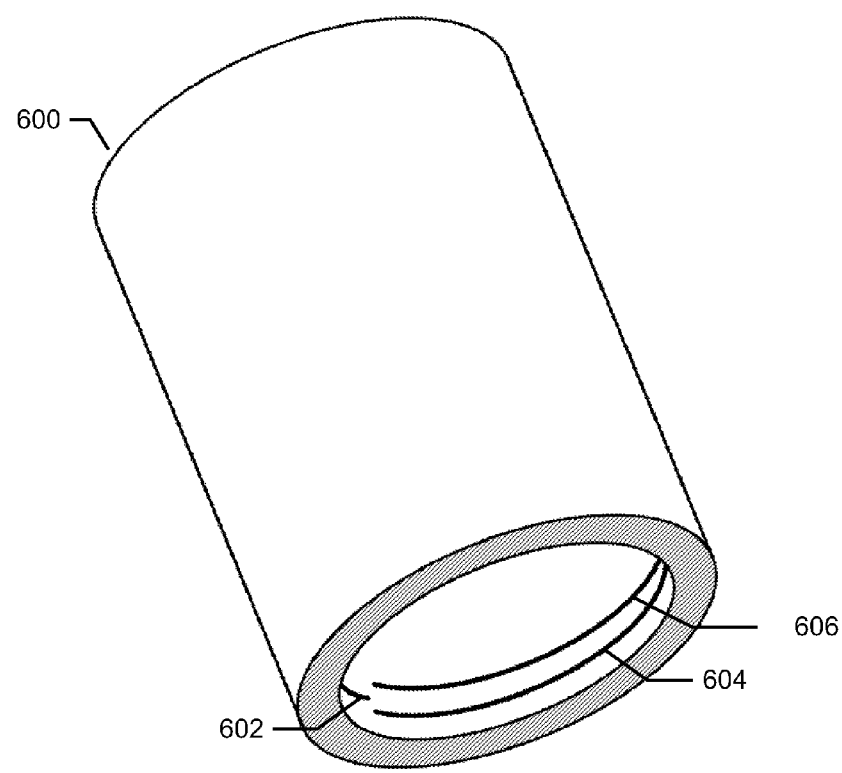
FIGS. 6A and 6B illustrate another embodiment of the invention that uses a nested offset rib structure that seals the opening of invention pouch or other device.
Figure 8:
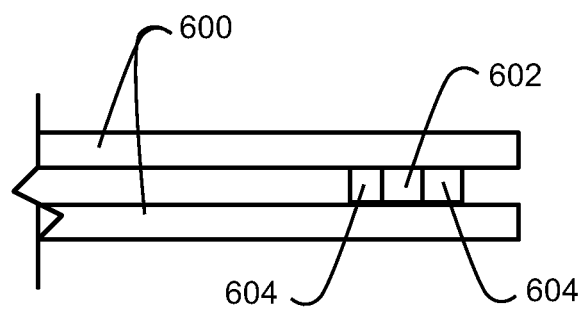
FIGS. 8A and 8B are cross-sectional views illustrating interlocking ribs.

FIG. 6A illustrates yet another embodiment of a security pouch 600 showing the pouch with three rib structures 602, 604 and 606 used to seal the opening of the pouch. Two rib structures, 604 and 606, are placed on the same side of the pouch in parallel and separated by a distance that is approximately equal to the thickness of the third rib structure 602. Rib structures 604 and 606 extend inwardly into the opening within security pouch 600. The third rib structure 602 is placed on the opposite side of the pouch as the rib structures 604 and 606, and also extends inwardly into the opening within security pouch 600. Rib structure 602 is placed parallel to rib structures 604 and 606 such that when the pouch is closed, the rib structure 602 snugly nests between and in contact with rib structures 604 and 606 to complete the seal (see FIGS. 8A and 8B).

Figure 6B:
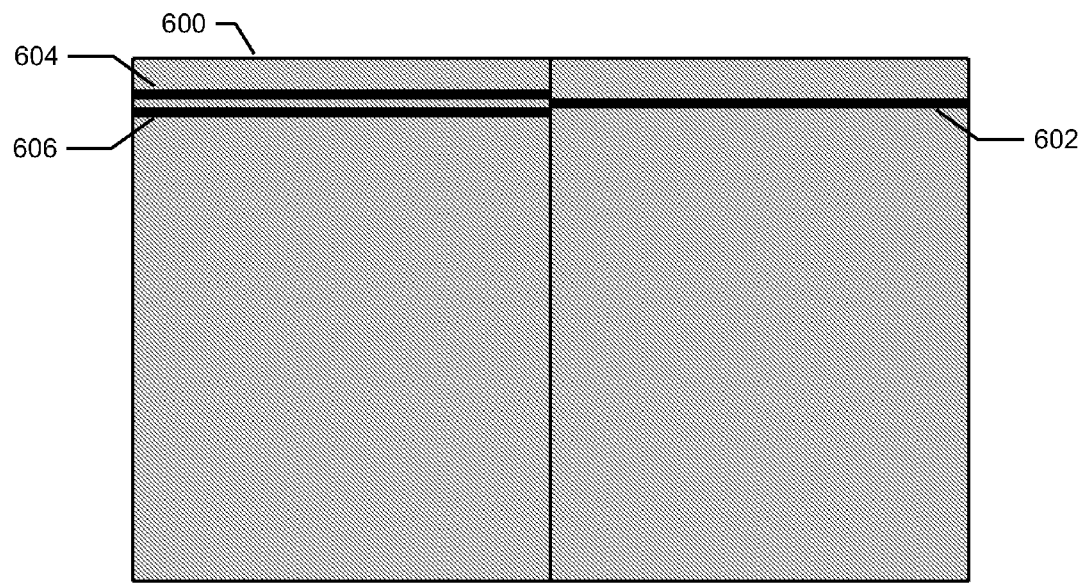
Figure 9:
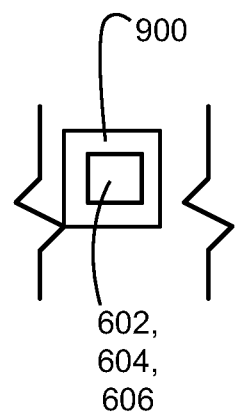
FIG. 9 is a cross-sectional view of a rib covered in a shielding material.

FIG. 6B is another view of security pouch 600 with one edge opened up to show the internal positions of rib structures 602, 604 and 606. In some embodiments, the rib structures 602, 604 and 606 are made from braided cotton rope and covered with two layers of nickel/copper ripstop. In other embodiments, the rib structures 602, 604 and 606 are made from materials such as rolled nickel/copper ripstop, metal wire, braided cord/rope and leather cord. In additional embodiments, the rib structures 602, 604 and 606 could be magnetic structures covered in shielding material 900 (see FIG. 9). In this embodiment, additional sealing effectiveness would be provided due to the magnetic closure capability of the rib structures 602, 604 and 606. In other embodiments, the rib structures can be constructed with any other cross-sectional shape, such as a square cross section, triangular, hexagonal, or any other shape.

Figure 7:
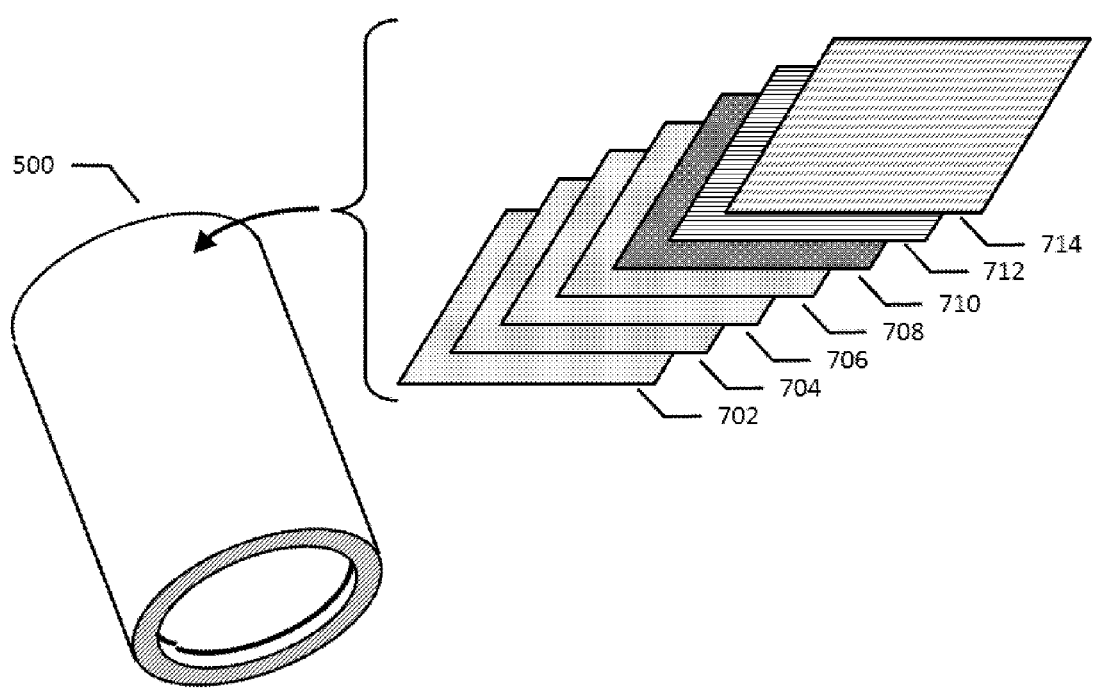
FIG. 7 illustrates the different material layers used in the construction of an embodiment of the security pouch or other device.

FIG. 7 illustrates an embodiment depicting the different material layers used to construct the security pouch 500. In this embodiment, seven layers are used to construct the security pouch. Of these seven layers, the innermost four layers 702, 704, 706, 708 are comprised of nickel/copper ripstop shielding material. These layers shield a broad spectrum of electronic signals. The fifth layer 710 in this embodiment is composed of a material, such as foil, that blocks near-field communication (NFC) and RF Identification (RFID) signals. Materials such as that marketed under the name Cryptalloy™ can be used to construct this layer. The sixth layer 712 is thin foam padding, while the seventh and outermost layer 714 is material such as vinyl, leather or canvas that is used to construct the external casing or shell of the shield. In alternate embodiments, an additional inner liner layer may be provided as the innermost layer of the security pouch.

Further, the opening and closing actions of rib structures 502 and 504 are completely reversible and reusable, unlike certain types of seals that are single-use or limited-use. Additionally, the magnetic closure capability gives the security pouch a self-sealing capability, as compared to other mechanisms that require the user to physically operate a zipper, Velcro tab, and the like to close the security pouch.

In yet another embodiment, the security pouch is made from a material that is capable of eliminating bacteria. One example of such material is silver. Silver can effectively eliminate 99.9% of bacteria in less than one hour of exposure and can inhibit the growth of odor-causing bacteria and fungi. Another example of such material is a fabric that contains silver fiber. This fabric is made from blending silver fiber with other fibers, such as cotton, polyester or wool. As result, when a mobile device is encased and in direct contact with the shield, the silver sanitizes the device. Further, because silver has high conductivity, both of the above materials may block electronic signals and disable a mobile device's tracking function.

In particular embodiments, the security pouch shields a wide range of signal frequencies, including RFID/NFC frequency ranges and all relevant signal strengths. The security pouch also shields CDMA, GSM, DCS, PHS, 3G, 4G, WiFi, Bluetooth, and GPS signals. Additionally, the security pouch is capable of blocking signals from any carrier, on any electronic device, in any geographic location. The security pouch also shields against EMF radiation, static shock, identity theft, cell phone spying, GPS tracking, RFID chip access, smart key access, and other electronic device access.

Those skilled in the art will understand that different combinations and permutations of different layers may be used to effect the ultimate goal of enveloping a device in the shield material, whether there are intermediary layers used for different reasons. For example, a security pouch may include an outer lining, and/or an inner lining, where the outer lining allows for a user to hold the pouch without contacting the lining, and the inner lining allows the device to be held without directly contacting the shield material. In another example, the shield may actually contact the device in order to allow for anti-bacterial or other affects to take place. The invention, however, is defined by the appended claims and their equivalents, and also possible future claims and their equivalents.

The invention claimed is:

1. A pouch for holding a mobile device, comprising:
   a shield defining a cavity;
   a covering configured to envelope the shield such that a user may hold the pouch without contacting the shield;
   a liner positioned within the cavity of the shield, the liner defining an opening; and
   a seal including a set of rib structures attached to the liner and configured to fully encase the mobile device to prevent electronic signals from reaching the mobile device and to prevent the electronic signals transmitted by the mobile device from reaching other devices outside the pouch, the set of rib structures including a first rib structure positioned on a first side of the opening and two second rib structures positioned on a second side of the opening opposite the first rib structure, the first rib structure and the two second rib structures comprising an electromagnetic shielding material, the first rib structure being positioned between and contacting the two second rib structures when the opening is closed effective to block the electronic signals.

2. A pouch according to claim 1, wherein the shield is effective to cause a mobile device positioned in the pouch to be blocked from RF signals and stopped from pinging and revealing its location.

3. A pouch according to claim 1, wherein the shield includes fabric having silver embedded within.

4. A pouch according to claim 1, wherein the shield is made from one of silver, zinc, copper and nickel.

5. A pouch according to claim 1, wherein the shield is made from loaded material silver to disinfect a mobile device as well as block electrical signals while encased within the pouch.

6. A pouch according to claim 1, wherein the shield is made from blending silver fiber and other fibers, including at least one of cotton, polyester, and wool, in order to disinfect a mobile device as well as block electrical signals while encased within the pouch.

7. A pouch according to claim 1, wherein the seal is made from a magnetic strip.

8. A pouch according to claim 1, wherein the at least one first rib structure and at least two second rib structures are parallel to one another when the seal is closed.

9. A pouch according to claim 1, wherein the at least one first rib structure and at least two second rib structures comprising the seal include a first rib and at least two second ribs covered in shielding material.

10. A pouch according to claim 1, wherein the shield includes a plurality of layers of shielding material disposed on top of one another.

11. A pouch according to claim 1, wherein the shield includes at least one layer of shielding material and at least one layer of shielding foil substantially surrounding the shielding material, the shielding layer including at least one of nickel, zinc, silver, and copper.

12. A pouch for holding a mobile device, comprising:
    an inner lining configured to envelope a mobile device;
    a shield configured to envelope the inner lining;
    a covering configured to envelope the shield such that a user may hold the pouch without contacting the shield;
    a plurality of magnets adjacent the inner lining and configured to maintain the pouch in a closed position;
    a first rib structure positioned on a first side of the inner lining; and
    two second rib structures positioned on a second side of the inner lining opposite the first side, wherein the first rib structure extends inwardly from the first side and the two second rib structures extend inwardly from the second side of the inner lining of the pouch, and wherein the first rib structure is positioned between and contacts the two second rib structures, the first rib structure and the two second rib structures comprising an electromagnetic shielding material such that the two second rib structures having the first rib structure positioned between the two second rib structures prevent electronic signals from reaching the mobile device when the pouch is in the closed position and block radio frequency (RF) signals from the mobile device to stop the mobile device from pinging and revealing its location.

13. A pouch according to claim 12, wherein the shield is made of at least one of silver, zinc, copper and nickel.

14. A pouch according to claim 12, wherein the shield is made from silver effective to disinfect a mobile device positioned within the pouch as well as block electrical signals while the mobile device is encased within the pouch.

15. A pouch according to claim 12, wherein the shield is made from blending silver fiber and other fibers, including at least one of cotton, polyester, and wool, to disinfect a mobile device as well as block electrical signals while encased within the pouch.

16. A pouch according to claim 12, wherein the first rib structure is made from a magnetic strip and the two second rib structures are made from a magnetic material.

17. A pouch according to claim 12, wherein the first rib structure and two second rib structures lie adjacent and parallel to one another when the seal is closed.

18. A pouch according to claim 12, wherein t the at least one first rib structure and at least two second rib structures include a first rib and at least two second ribs covered in shielding material.

19. A pouch according to claim 12, wherein the shield includes at least one layer of shielding material and at least one layer of shielding foil substantially surrounding the shielding material, the shielding material comprising at least one of nickel and copper.

* * * * *